United States Patent
Smith et al.

(10) Patent No.: US 6,932,843 B2
(45) Date of Patent: Aug. 23, 2005

(54) APPARATUS AND METHOD FOR THE IN-SITU FORMATION OF A STRUCTURAL PROSTHESIS

(75) Inventors: Stephen A. Smith, Fresno, CA (US); T. Wade Fallin, Hyde Park, UT (US)

(73) Assignee: MedicineLodge, Inc., Logan, UT (US)

( * ) Notice: Subject to any disclaimer, the term of this patent is extended or adjusted under 35 U.S.C. 154(b) by 0 days.

(21) Appl. No.: 10/255,161

(22) Filed: Sep. 25, 2002

(65) Prior Publication Data

US 2004/0059417 A1 Mar. 25, 2004

(51) Int. Cl.⁷ .................................................. A61F 2/44
(52) U.S. Cl. .................................................. 623/17.11
(58) Field of Search ......................... 623/17.11, 17.12, 623/17.16; 606/92, 94, 61, 86, 87, 88, 93

(56) References Cited

U.S. PATENT DOCUMENTS

| | | | |
|---|---|---|---|
| 3,875,595 A | | 4/1975 | Froning |
| 5,002,576 A | | 3/1991 | Fuhrmann et al. |
| 5,146,933 A | * | 9/1992 | Boyd .......................... 128/899 |
| 5,549,679 A | | 8/1996 | Kuslich |
| 5,556,429 A | * | 9/1996 | Felt ............................. 128/898 |
| 5,571,189 A | | 11/1996 | Kuslich |
| 5,645,597 A | | 7/1997 | Krapiva |
| 5,827,289 A | | 10/1998 | Reiley et al. |
| 5,888,220 A | * | 3/1999 | Felt et al. ..................... 128/898 |
| 6,132,468 A | | 10/2000 | Mansmann |
| 6,183,518 B1 | | 2/2001 | Ross et al. |
| 6,187,048 B1 | | 2/2001 | Milner et al. |
| 6,248,131 B1 | * | 6/2001 | Felt et al. ................. 623/17.12 |
| 6,258,195 B1 | * | 7/2001 | Holman et al. ............. 156/166 |
| 6,395,034 B1 | | 5/2002 | Suddaby |
| 6,436,143 B1 | | 8/2002 | Ross et al. |
| 6,443,988 B2 | * | 9/2002 | Felt et al. ................. 623/17.12 |
| 6,582,446 B1 | * | 6/2003 | Marchosky ................. 606/167 |
| 2001/0004710 A1 | | 6/2001 | Felt et al. |
| 2001/0032019 A1 | | 10/2001 | Van Dyke et al. |
| 2002/0045942 A1 | | 4/2002 | Ham |
| 2002/0049498 A1 | | 4/2002 | Yuksel et al. |
| 2002/0055757 A1 | * | 5/2002 | Torre et al. ................. 606/192 |
| 2002/0156482 A1 | | 10/2002 | Scribner et al. |

* cited by examiner

*Primary Examiner*—Pedro Philogene
(74) *Attorney, Agent, or Firm*—Workman Nydegger (57) ABSTRACT

An apparatus for in-situ formation of a structural prosthesis includes a tubular member having a proximal end and an opposing distal end. A balloon having a compartment is disposed on the tubular member such that a curable biomaterial can be selectively delivered to the compartment of the balloon through the tubular member. A line is disposed on or in the wall of the balloon to facilitate at least partial severing of the wall of the balloon after the biomaterial has at least partially cured therein such that the balloon can be selectively removed from around the at least partially cured biomaterial, thereby forming a structural prosthesis.

42 Claims, 12 Drawing Sheets

APPARATUS AND METHOD FOR THE IN-SITU FORMATION OF A STRUCTURAL PROSTHESIS

CROSS-REFERENCE TO RELATED APPLICATIONS

Not applicable.

BACKGROUND OF THE INVENTION

1. The Field of the Invention

The present invention relates generally to apparatus and methods for the in-situ formation of structural prostheses and particularly for in-situ formation of structural prostheses for the spine.

2. The Relevant Technology

Figure 1:
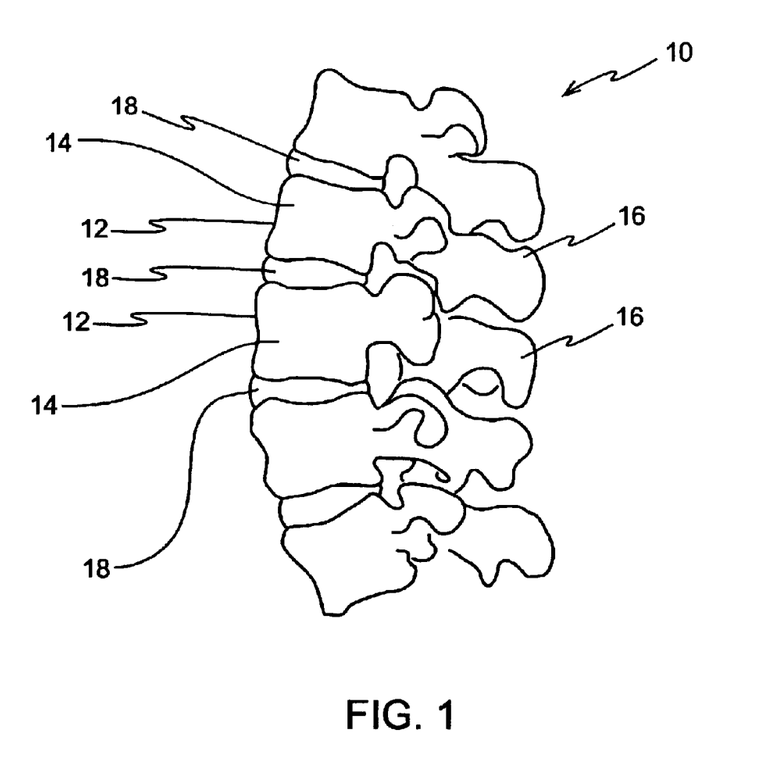
FIG. 1 is an elevated side view of a section of a spinal column.
Figure 2:
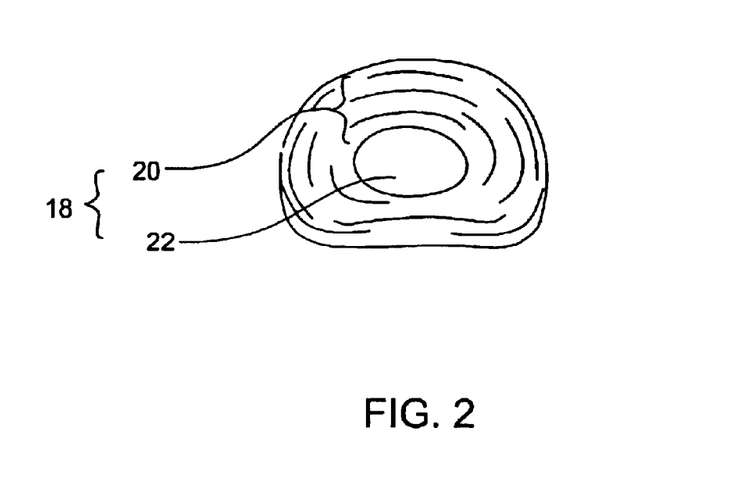
FIG. 2 is a top plan view of an intervertebral disc.

Depicted in FIG. 1 is a section of a spinal column 10. Spinal column 10 comprises a plurality of stacked vertebrae 12. In general, each vertebrae 12 is comprised of a substantially cylindrical vertebral body 14 having a spinous process 16 projecting therefrom. Spinal column 10 further comprises an intervertebral disc 18 located between each adjacent vertebrae 12. As depicted in FIG. 2, intervertebral disc 18 generally consists of an outer ring structure called the annulus fibrosus 20. Annulus Fibrosus 20 encircles a gelatinous central core called the nucleus pulposus 22. Intervertebral disc 18 is comprised of collagen with annulus fibrosus 20 being significantly stiffer than the gelatinous nucleus pulposus 22. In this regard, annulus fibrosus 20 functions in part as a wall that retains nucleus pulposus 22. Intervertebral disc 18 together with the two adjacent vertebrae 12 form a joint motion segment that serves to provide limited motion in forward bending, lateral bending, and rotation.

Degenerative discs 18 can cause debilitating back pain. Discs 18 progressively degenerate during aging, characterized by dehydration and hardening of the nucleus pulposus 22 and the annulus fibrosus 20. The annulus fibrosus 20 may weaken and bulge, or may develop fissures that allow the nucleus pulposus 22 to extrude, commonly referred to as disc herniation. This bulging or extrusion often results in a decrease in disc height, thereby putting pressure on nerve roots and/or the spinal cord.

Various prefabricated prostheses have been developed to repair or replace a damaged intervertebral disc 18, including: prostheses for the replacement of the nucleus pulposus, commonly referred to as nucleus replacements; prostheses for the concurrent replacement of the annulus fibrosis, commonly referred to as a total disc replacement; and prostheses in the form of cages filled with osteogenic materials, commonly referred to as interbody fusion devices. These prefabricated prostheses are commercially offered in a limited number of sizes, limiting the surgeon's ability to precisely restore the disc height for individual patients. Furthermore, most of these prostheses require the creation of a surgical incision at least large enough to pass the implant to the site of repair. Surgical incisions cause disruptions and damage to various skin, muscle, tendon and ligament structures that extend the time of recover and rehabilitation for patients and that compromise the function of the violated anatomical structures.

More recently, disc replacements have been developed that use flowable biomaterials that harden in-situ to form a replacement nucleus pulposus. Forming a prosthesis in-situ from a flowable biomaterial potentially facilitates a minimally invasive approach (i.e., no resection of tissue) to the repair site, thereby minimizing the damage to anatomical structures and enabling much quicker patient recoveries to full function. However, nucleus replacements formed from flowable biomaterials either require an implantable mold, such as that disclosed by U.S. Pat. Nos. 3,875,595 to Froning and U.S. Pat. No. 5,549,679 to Kuslich and U.S. Patent Application Publication No. 2001/004710 to Felt et al., or utilize the existing annulus fibrosus as the mold as disclosed in U.S. Patent Application Publication No.'s U.S. 2002/0049498 to Yussel et al. and U.S. 2002/0045942 to Ham, and U.S. Pat. No. 6,183,518 to Ross et al.

Several disadvantages exist with both the implantable mold and the use of the existing annulus fibrosus as the mold. An implantable mold cavity creates an additional interface between the mold and the flowable biomaterial which may be subject to interfacial shear stresses producing interfacial motions that create wear debris and compromise the structural integrity of both the mold and core formed from the flowable biomaterial. Using the existing annulus fibrosus as the mold is also problematic in that the annulus fibrosus is often degenerated so as to have one or more fissures extending therethrough. Such fissures allow the injected flowable biomaterial to escape.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to apparatus and methods for the in-situ formation of structural prosthesis. In the embodiments depicted, such prosthesis are formed so as to replace all or a portion of an intervertebral disc or are formed within a vertebral body so as to reinforce the vertebral body or to restore the height of a compressed vertebral body. In general, the apparatus and methods use a balloon as a mold. The balloon is surgically positioned at the location for the structural prosthesis. Once positioned, the balloon is filled to a predetermined extent with a curable biomaterial. The amount of biomaterial used corresponds to the desired size for the structural prosthesis. Once the biomaterial has at least partially cured, the balloon is removed leaving the biomaterial to fully cure into the structural prosthesis.

Figure 3:
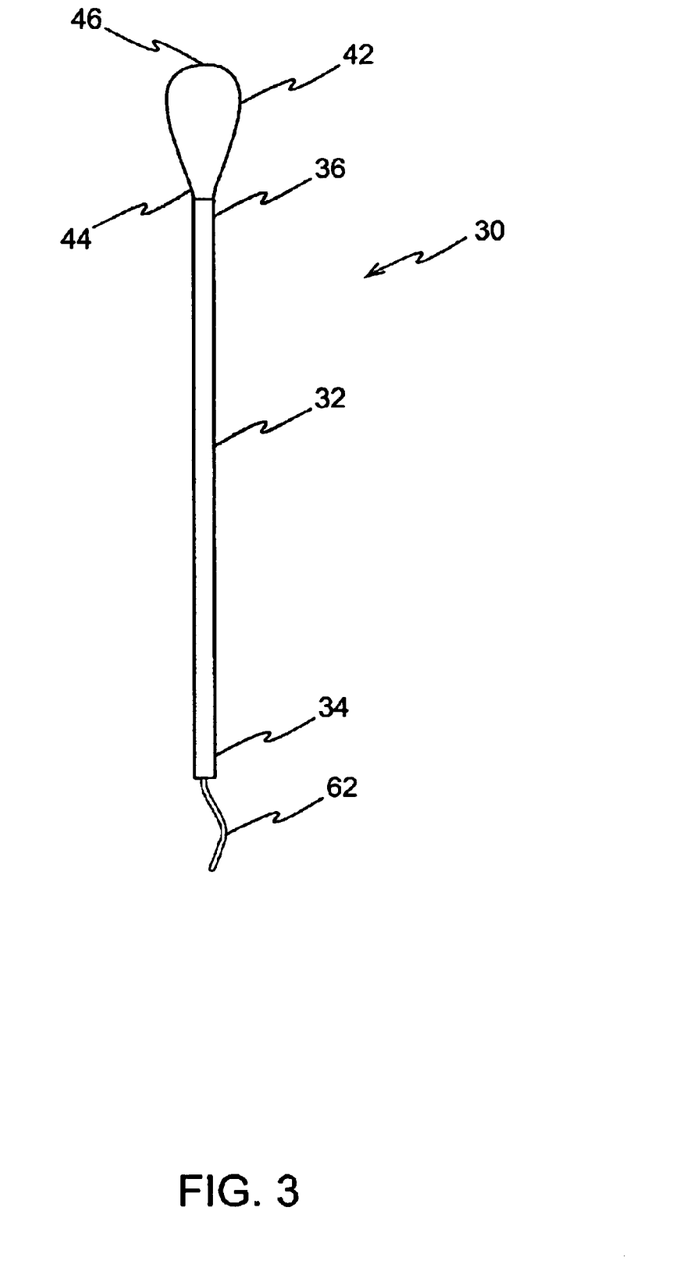
FIG. 3 is an elevated side view of an in-situ prosthesis formation apparatus.
Figure 4:
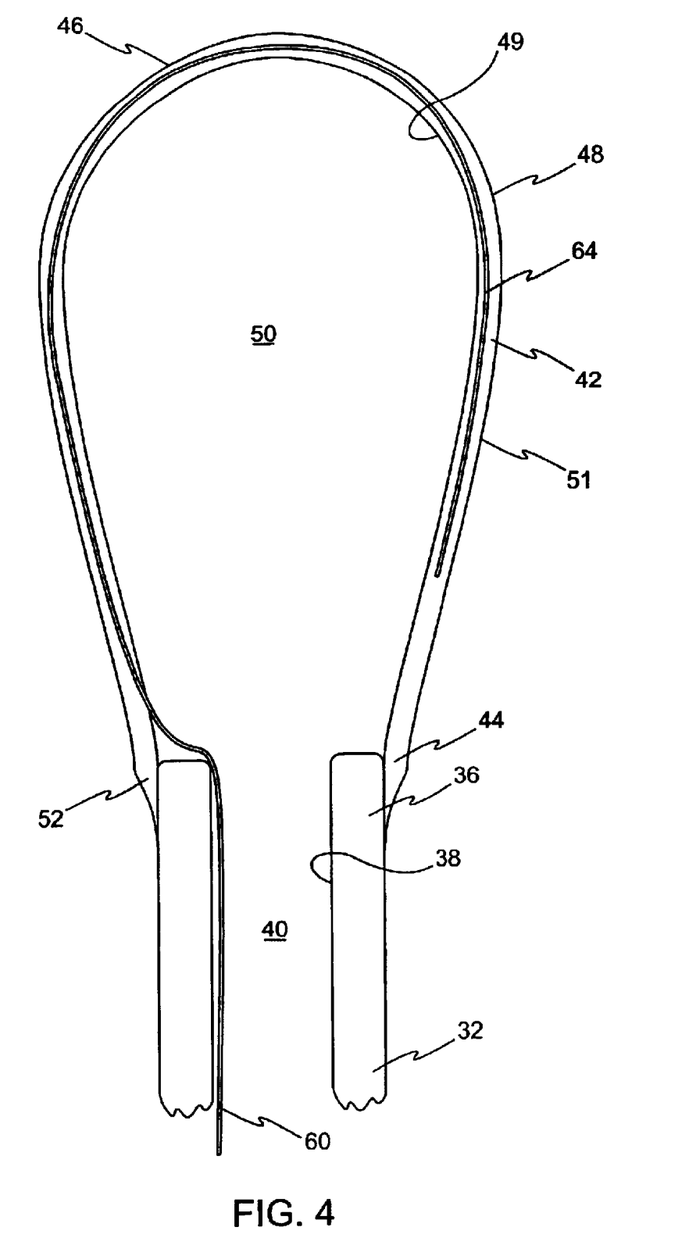
FIG. 4 is an enlarged cross sectional side view of the distal end of the apparatus shown in FIG. 3.

Depicted in FIGS. 3 and 4 is one embodiment of an in-situ prosthesis formation apparatus 30 incorporating features of the present invention. Apparatus 30 comprises an elongated tubular member 32 having a proximal end 34 and an opposing distal end 36. Tubular member 32 has an interior surface 38 bounding a passageway 40 (FIG. 4) longitudinally extending therethrough. Tubular member 32 can be rigid or flexible and can be made from plastic, metal, or any other material capable sterilization for medical use. For example, tubular member 32 can comprise a flexible catheter or a rigid cannula.

Mounted at distal end 36 of tubular member 32 is a balloon 42. Balloon 42 has a proximal end 44 and terminates at an opposing distal end 46. Balloon 42 is comprised of a boundary wall 48 having an exterior surface 51 and an interior surface 49. Interior surface 49 bounds a chamber 50. An annular mouth 52 is formed at proximal end 44 of balloon 42 and provides fluid communication with chamber 50. Mouth 52 is coupled in sealed engagement with distal end 36 of tubular member 32 so that passageway 40 of tubular member 32 is in fluid communication with chamber 50 of balloon 42. For example, mouth 52 can be coupled with tubular member 32 by welding, adhesive, clamp, or other conventional fastening techniques. Balloon 42 can also be integrally molded with tubular member 32 so that they form a one-piece member.

In one embodiment, balloon 42 is made of a resiliently expandable material. Accordingly, as balloon 42 is filled, it initially inflates to a non-stretched configuration. As balloon 42 is further filled, boundary wall 48 resiliently stretches so as to allow balloon 42 to expand to a larger configuration. In an alternative embodiment, balloon 42 can be made of a flexible static material. For example, balloon 42 can be comprised of one or two or more sheets of polymeric material that are seamed together. In this embodiment, balloon 42 inflates to a predefined configuration but cannot significantly expand beyond that configuration. By using seamed sheets of static material, balloon 42 can be more easily configured to inflate into any desired configuration.

Balloon 42 is typically made of materials commonly known in the art, such as those used in balloon catheters, balloon angioplasty devices, inflatable cuffs used in endotracheal devices, and balloons used as bone tamps for vertebral body augmentation procedures. Examples of suitable materials for balloon 42 are natural materials or synthetic materials, such as polyurethane, polyolefin, polycarbonate, polyethylene, polyethylene terephtalate, tetrafluoroethylene, or copolymers thereof. The material for balloon 42 can also be reinforced with fibers or other additives to adjust the strength, flexibility, elasticity, and/or other properties of balloon 42. The additives can also be used to provide desired shape constraints. Suitable materials for fiber reinforcement include: carbon fibers, glass fibers, nylon fibers, polyethylene fibers, polyester fibers, and the like. Depending on its intended use, balloon 42 can be configured to expand into any desired configuration.

As will be discussed below in greater detail, during use balloon 42 is surgically positioned at a location for the structural prosthesis. Once positioned, balloon 42 is selectively filed with a flowable, curable biomaterial. The biomaterial is injected into balloon 42 by way of tubular member 32. By way of example and not by limitation, the biomaterial can comprise curable hydrogel, polyurethane, calcium phosphate, calcium sulfate, acrylic, carbonate, or any other suitable material that is biocompatible. In one embodiment, the biomaterial has a cure time of less than about 30 minutes and preferably less than about 5 minutes.

In one embodiment of the present invention, means are provided for at least partially severing boundary wall 48 of balloon 42 after the biomaterial has at least partially cured therein such that balloon 42 can be selectively removed from around the at least partially cured biomaterial. By way of example and not by limitation, depicted in FIG. 4 is a line 60 having a proximal end 62 (FIG. 3) and an opposing distal end 64. Depending on the desired embodiment, line 60 or other lines disclosed herein can be comprised of a metal wire, suture, plastic line, small diameter cord or cable, optical cable, or any other small diameter line.

In the embodiment depicted, line 60 extends through passageway 40 of tubular member 32 such that at least a portion of proximal end 62 of line 60 freely projects proximal of tubular member 32. Furthermore, at least a portion of distal end 64 of line 60 is disposed within balloon 42. More specifically, distal end 64 of line 60 is embedded within boundary wall 48 of balloon 42 so as to follow a substantially semi-circular path extending from proximal end 44 of balloon 42, to distal end 46, and then back toward proximal end 44 on the opposing side of balloon 42. Line 60 is configured such that when proximal end 62 is pulled, line 60 is pulled out of balloon 42 so as to at least partially sever boundary wall 48 along the track of line 60. Once boundary wall 48 is at least partially severed, tubular member 32 is retracted from its surgical placement. As tubular member 32 is retracted, balloon 42 opens along the at least partially severed track of line 60 so that balloon 42 retracts from around the at least partially set biomaterial disposed therein. Balloon 42 is then fully removed with tubular member 32, leaving the biomaterial implanted so as to fully cure into the structural prosthesis.

Line 60 can be configured in a variety of different ways to facilitate severing of boundary wall 48. For example, line 60 can be embedded within boundary wall 48 such that by simply removing line 60, boundary wall 48 is sufficiently weakened so that when balloon 42 is pulled on by tubular member 32, balloon 42 completely severs. Alternatively, line 60 can be embedded within boundary wall 48 such that line 60 tears boundary wall 48 as line 60 is removed. In yet another embodiment, line 60 can be made with a sharpened edge, a roughened surface, or sufficiently thin so that line 60 cuts through boundary wall 48 as line 60 is removed. In still other embodiments, a sharpened tooth, hook, spike or other structure can be placed at one or more locations along line 60 so as to cut boundary wall 48 as line 60 is removed. In this embodiment, line 60 can be configured to efficiently cut both outward and inward.

In all of the embodiments discussed herein, it is appreciated that line 60 can either sever completely through boundary wall 48 or sever a portion of boundary wall 48 sufficiently to weaken it so that boundary wall 48 completely severs as balloon 42 is retracted. Although line 60 is shown extending through passageway 40 of tubular member 32 and embedded within boundary wall 48, in other embodiments, line 60 can extend on the exterior of tubular member 32. Likewise line 60 can be positioned on exterior surface 51 or interior surface 49 of balloon 42. Furthermore, in contrast to having a single line 60 that substantially bisects balloon 42, two or more lines 60 can be used to sever boundary wall 48 at different orientations. For example, two lines can extending on opposing sides of balloon 42 and intersect at distal end 46.

Figure 5:
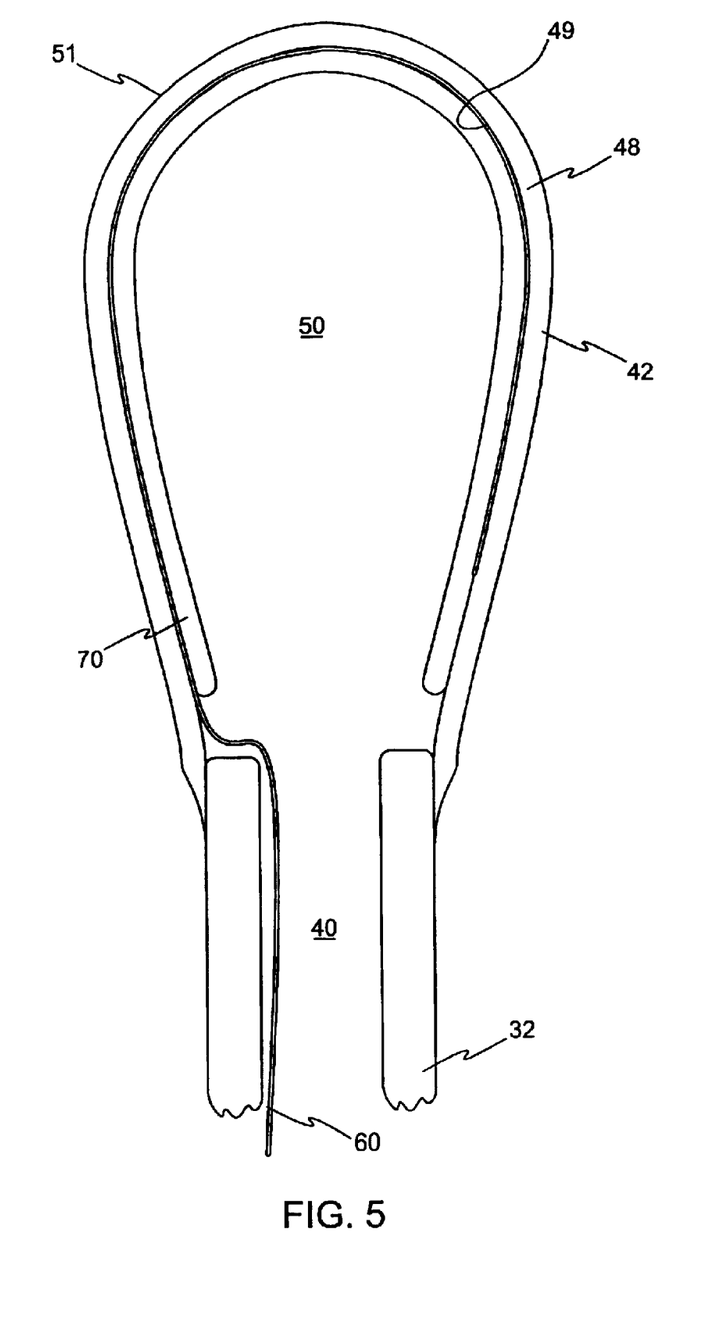
FIG. 5 is an enlarged cross sectional side view of an alternative embodiment of the distal end of the apparatus shown in FIG. 3.

Depicted in FIG. 5, in contrast to line 60 being embedded with boundary wall 42, a support layer 70 is applied over line 60 so as to secure line 60 against interior surface 49 of balloon 42. Support layer 70 can be applied over all of interior surface 49 or only over the segment along line 60. Similarly, support layer 70 can be applied over exterior surface 51 of balloon 42 so as to secure line 60 against exterior surface 51. Support layer 70 can be comprised of an adhesive, tape, or any of the materials of which boundary wall 48 is comprised. Again, as discussed above, multiple lines 60 can be used. Furthermore, any of the different techniques discussed herein can be used for line 60 to facilitate severing of boundary wall 48.

Figure 6:
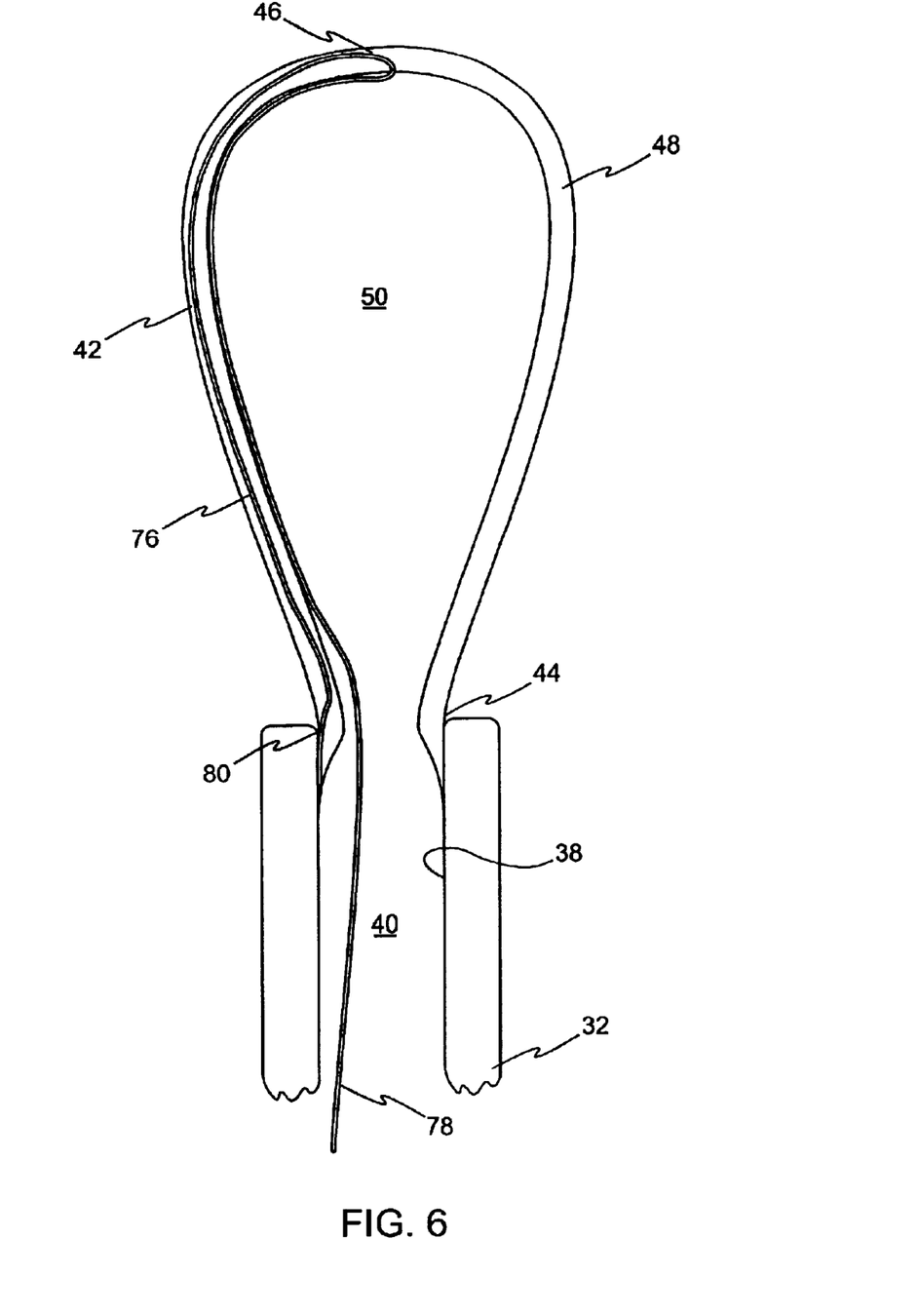
FIG. 6 is an enlarged cross sectional side view of another alternative embodiment of the distal end of the apparatus shown in FIG. 3.

Depicted in FIG. 6 is yet another alternative embodiment of the means for at least partially severing boundary wall 48 of balloon 42. As depicted therein, a line 76 is provided having a proximal end 78 and an opposing distal end 80. Proximal end 78 extends out through tubular member 32 while distal end 80 is secured to interior surface 38 of tubular member 32. Starting at the location where distal end 80 is secured to interior surface 38, line 76 extends into boundary wall 48 at proximal end 44 of balloon 42 and runs therein to distal end 46 of balloon 42. At distal end 46, line 76 extends out of boundary wall 48 and then freely passes out through tubular member 32. In this configuration, as proximal end 78 of line 42 is pulled proximally, line 42 cuts through the inwardly disposed portion of boundary wall 48. In modifications to this embodiment, distal end 46 can also extend out through passageway 40 where it is manually retained. Furthermore, two or more lines 76 can be used extending from opposing sides of balloon 42. In addition, line 76 can extend on exterior surface 51 of balloon 42 so as to completely cut through boundary wall 48 when line 76 is removed.

Figure 7:
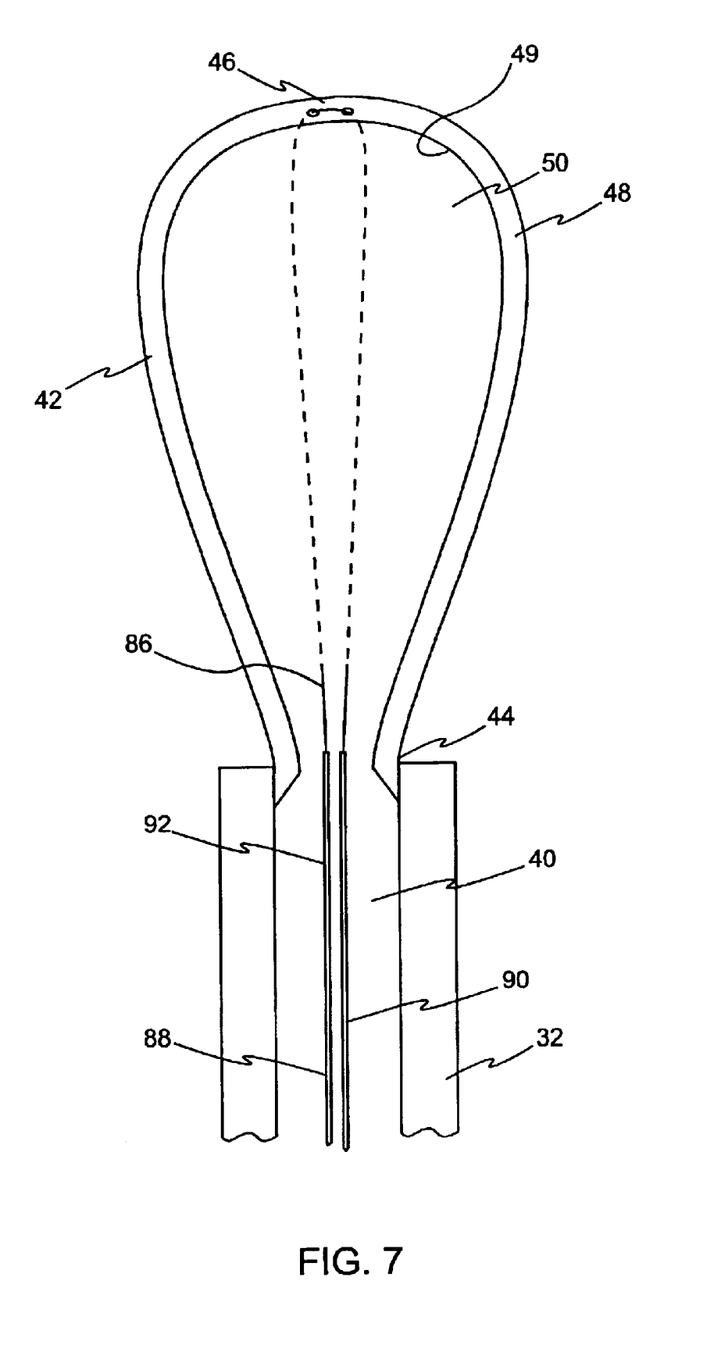
FIG. 7 is an enlarged cross sectional side view of still another alternative embodiment of the distal end of the apparatus shown in FIG. 3.

Depicted in FIG. 7 is yet another alternative embodiment of the means for at least partially severing boundary wall 48 of balloon 42. In this embodiment, a looped line 86 has a proximal end 88 and an opposing distal end 90. Starting from proximal end 88, line 86 extends through passageway 40 and into boundary wall 48 of balloon 42 at proximal end 44 thereof. Line 86 extends embedded with boundary wall 48 to distal end 46 and then back to tubular member 32. Line 86 then continues out through passageway 40. Insulation 92 covers lines 86 within passageway 40. During operation, an electrical current is passed through lines 86 so that the non-insulated portion of line 86 embedded within boundary wall 48 functions as a filament that heats up and melts the contacting boundary wall 48. Again, multiple lines 86 can be used to sever balloon 42 along different paths. In contrast to applying an electrical current to line 86, line 86 can be a conductor of radiofrequency or ultrasound energy, creating localized heating and melting of boundary wall 48. In still yet another embodiment, wire 86 can comprise a side firing laser that produces localized heating and melting of balloon 42.

In view of the foregoing, there are a variety of different line configurations that can be used to partially of completely sever boundary wall 48 of balloon 42 by techniques such as cutting, tearing, melting, and the like. It is appreciated that features and placements of the above described embodiments can be mixed and matched to form still other embodiments.

Figure 8:
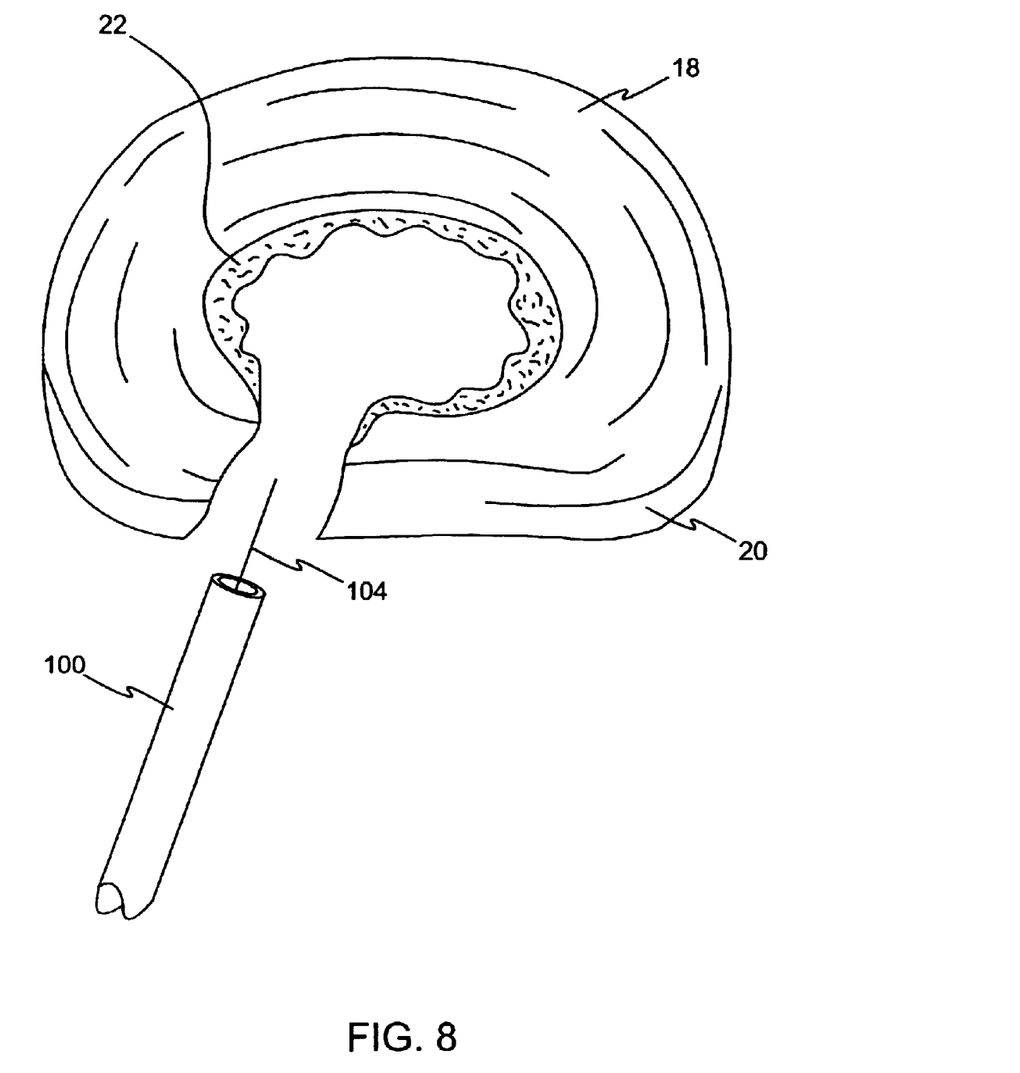
FIG. 8 is a perspective view of a working cannula being positioned at a degenerated intervertebral disc shown in FIG. 2 having a portion of the nucleus pulposus retracted.

As set forth below, the above apparatus and the alternatives thereto can be used in a variety of methods for forming in-situ structural prosthesis. By way of example, depicted in FIG. 8 is a intervertebral disc 18, as previously discussed above with regard to FIGS. 1–2, in which it is desired to replace the degenerated nucleus pulposus 22 with a structural prosthesis. A minimally invasive surgical approach is used to establish a percutaneous tract to the operative site with a guide wire 104. A working cannula 100 is then slid over guide wire 104 following which guide wire 104 is removed. Microsurgical techniques are then performed through cannula 100 using endoscopic visualization techniques to form an incision 98 through annulus fibrosus 20 and then substantially remove the degenerated nucleus pulposus 22 therethrough. In an alternative embodiment, a rupture in annulus fibrosus 20 may have already resulted in a substantial loss of nucleus pulposus 22 therethrough.

Figure 9:
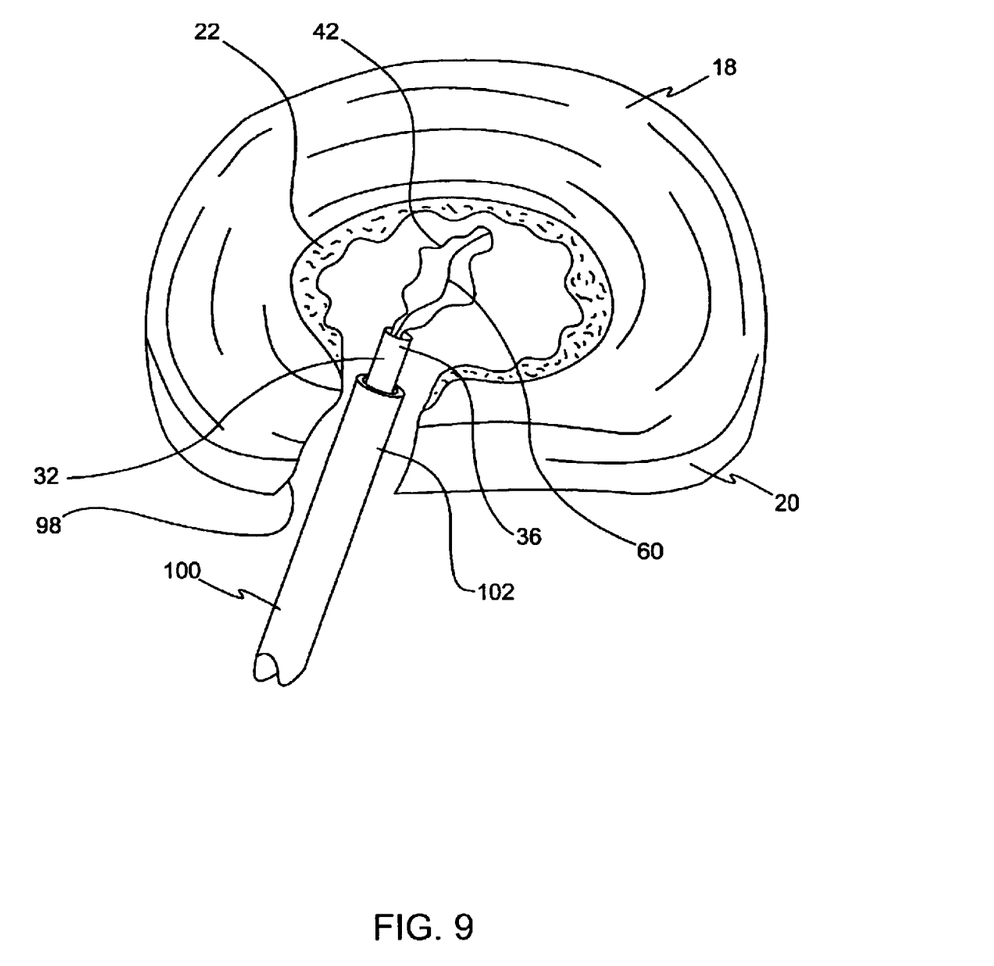
FIG. 9 is a perspective view of the apparatus shown in FIG. 3 inserted through the working cannula shown in FIG. 8 so that a balloon of the apparatus resides within the site of the retracted nucleus pulposus.

Turning to FIG. 9, with distal end 102 of a cannula 100 is communication with incision 98, distal end 36 of tubular member 32 is advanced down through cannula 100 so as to position deflated balloon 42 within the site of the resected nucleus pulposus 22. During insertion of tubular member 32, it is appreciated that balloon 42 can either freely extend distally of tubular member 32 or can be drawn into passageway 40 of tubular member 32. If balloon 42 is retained within passageway 40, a push rod or other structure can be used to push balloon 42 out of passageway and into the site of the resected nucleus pulposus 22. Alternatively, balloon 42 can be pushed out of tubular member 32 by the injection of biomaterial into tubular member 32 as discussed below.

Figure 10:
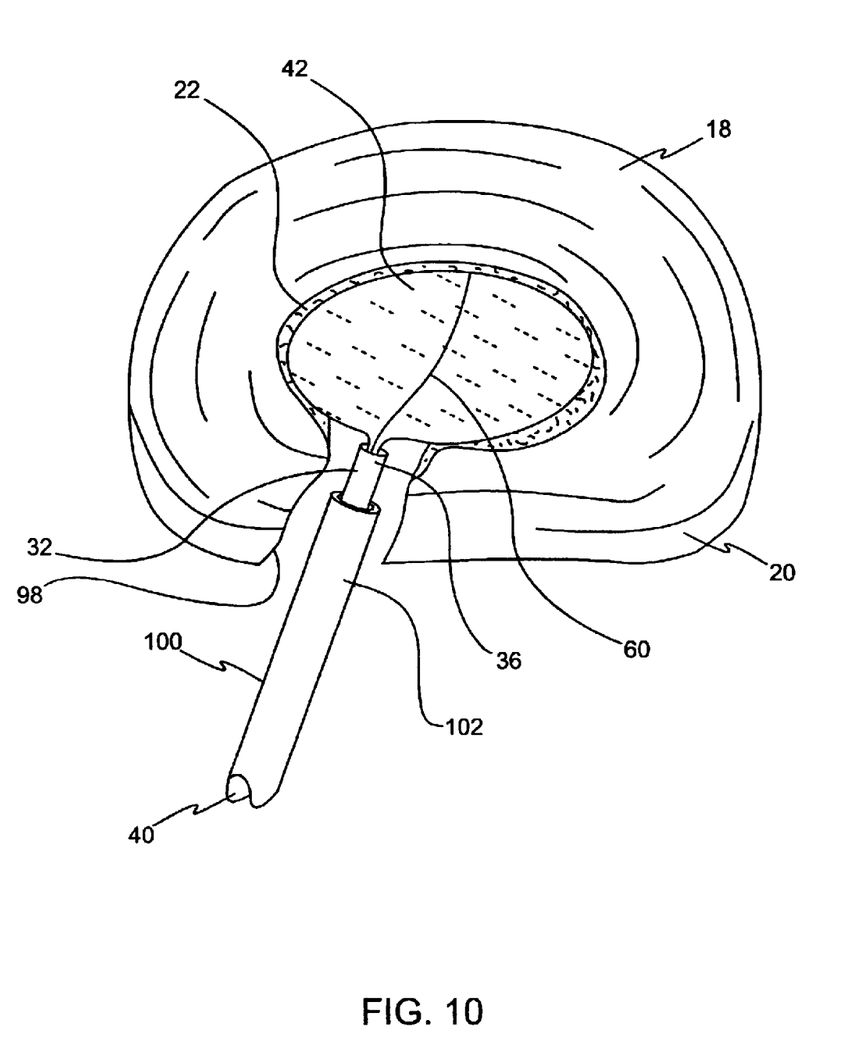
FIG. 10 is a perspective view of the balloon of FIG. 9 being filled with a biomaterial within the site of the retracted nucleus pulposus.

Turning to FIG. 10, once balloon 42 is properly position, the flowable, curable biomaterial 108 (FIG. 11) is passed down through tubular member 32 and into chamber 50 of balloon 42. Biomaterial 108 is injected until balloon 42 inflates and/or expands to the size corresponding to the original nucleus pulposus 22. In this embodiment, annulus fibrosus 20 functions as a wall that at least partially bounds the expansion of balloon 42 so that the proper amount of biomaterial 108 is injected. Unlike the prior art, however, balloon 42 helps to ensure that biomaterial 108 does not leak out through incision 98 or fissures in annulus fibrosus 20.

Figure 11:
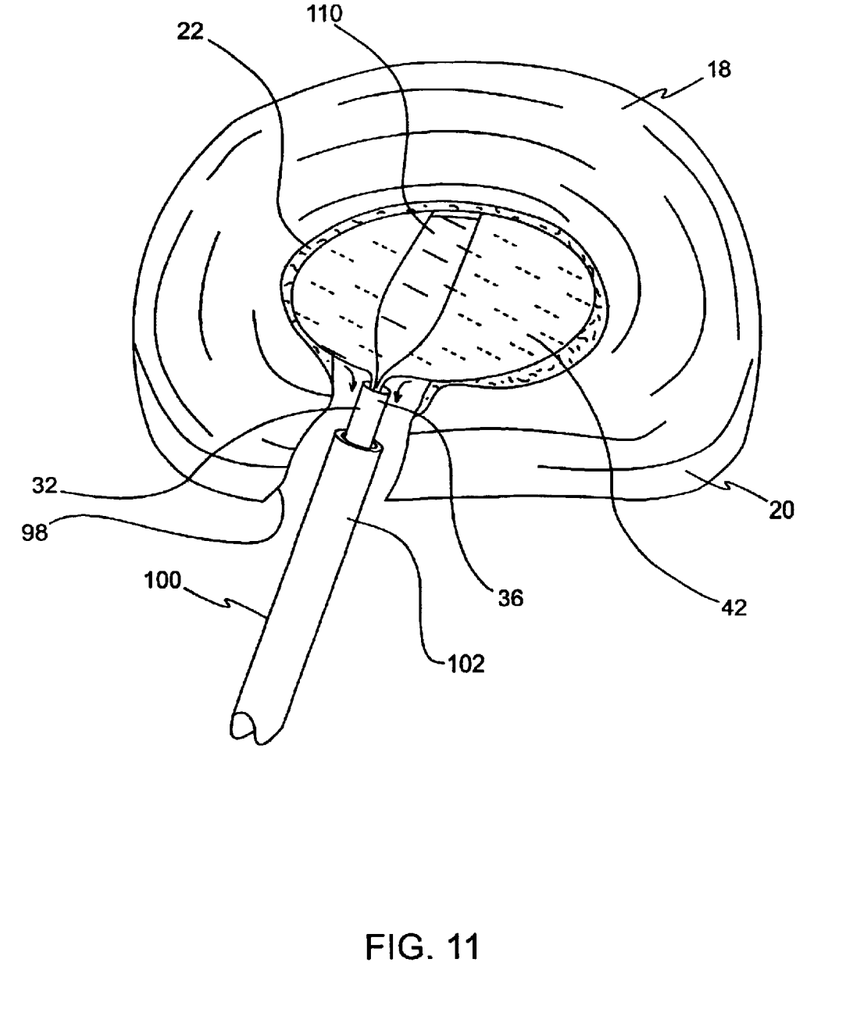
FIG. 11 is a perspective view of the balloon of FIG. 10 being severed for around the biomaterial therein.

As depicted in FIG. 11, once biomaterial 108 has at least partially cured within balloon 42, line 60 (FIG. 10), or other alternatives thereto as discussed above, is used to at least partially sever balloon 42. Tubular member 32 is then retracted causing balloon 42 to completely sever, if not previously completely severed, as shown by split 110. Balloon 42 is then fully retracted out with tubular member 32 so that severed balloon 42 passes around biomaterial 108, thereby leaving biomaterial 108 at the site of resected nucleus pulposus 22.

Figure 12:
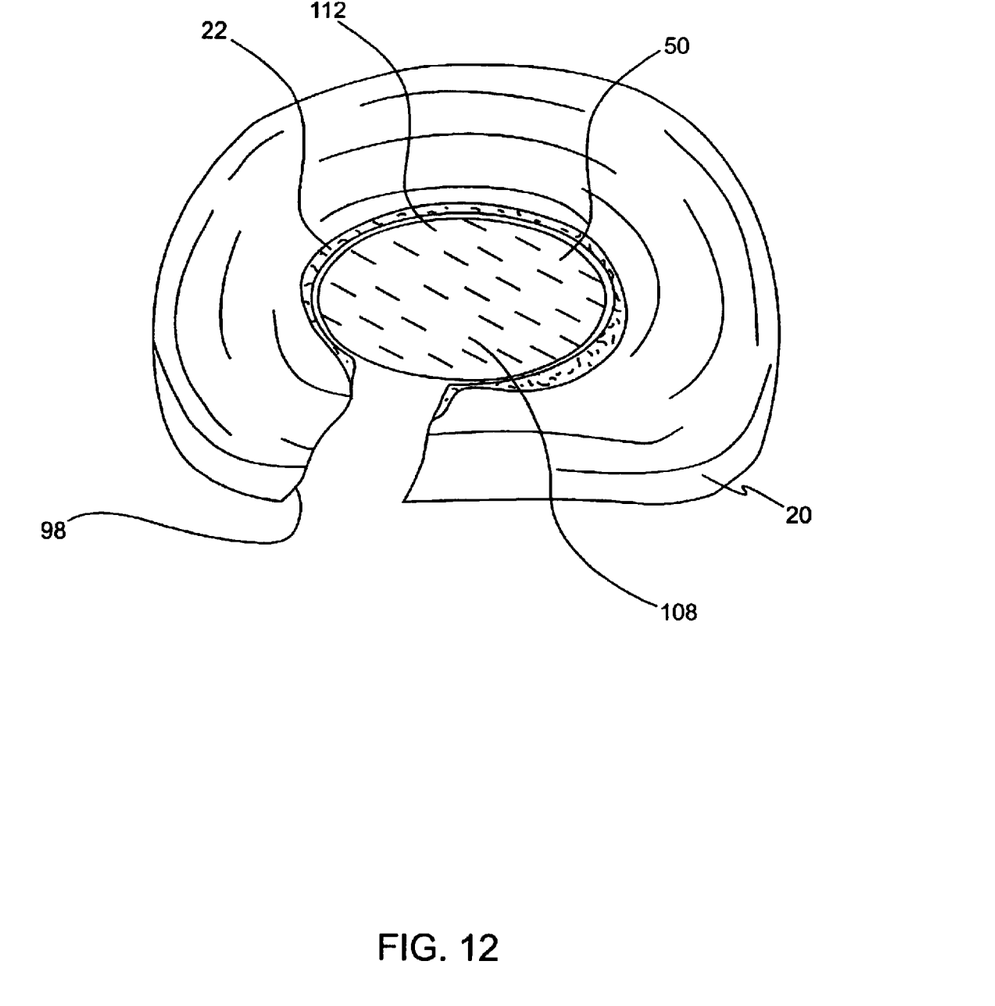
FIG. 12 is a perspective view of the biomaterial of FIG. 11 forming a structural prosthesis within the site of the retracted nucleus pulposus.

In turn, as depicted in FIG. 12, the remaining biomaterial finishes curing so as to form a structural prosthesis 112. In an alternative embodiment, it is noted that biomaterial 108 can be allowed to completely cure prior to use of line 60 or removal of balloon 42. Furthermore, it is also noted that prior to retraction of tubular member 32 and balloon 42, tubular member 32 is typically bent or otherwise manipulated so as to break the connection of the biomaterial within tubular member 32 to the biomaterial within the site of resected nucleus pulposus 22.

In contrast to the above discussed replacement of nucleus pulposus 22, the present apparatus and methods can also be used for a total or substantially total intervertebral disc replacement or for fusing together adjacent vertebrae. That is, microsurgical techniques are performed through cannula 100 to remove nucleus pulposus 22 and either all or a portion of annulus fibrosus 20. Using the same process as described above, balloon 42 is then placed as the site of the resected intervertebral disc. Balloon 42 is injected with the biomaterial until it extends to the size of the natural intervertebral disc or portion thereof resected. Once the biomaterial at least partially cures, the line is used to at least partially sever balloon 42. Tubular member 32 and balloon 42 are then retracted leaving the biomaterial to cure into the final structural prosthesis.

For the nucleus replacement and total disc replacement, materials with greater flexibility and compressibility are preferred, such as a hydrogel or polyurethane. For the interbody fusion device and the vertebral augmentation device, as discussed below, materials with greater stiffness and rigidity are preferred, such as calcium phosphate, calcium sulfate, acrylic, and carbonate.

Figure 13:
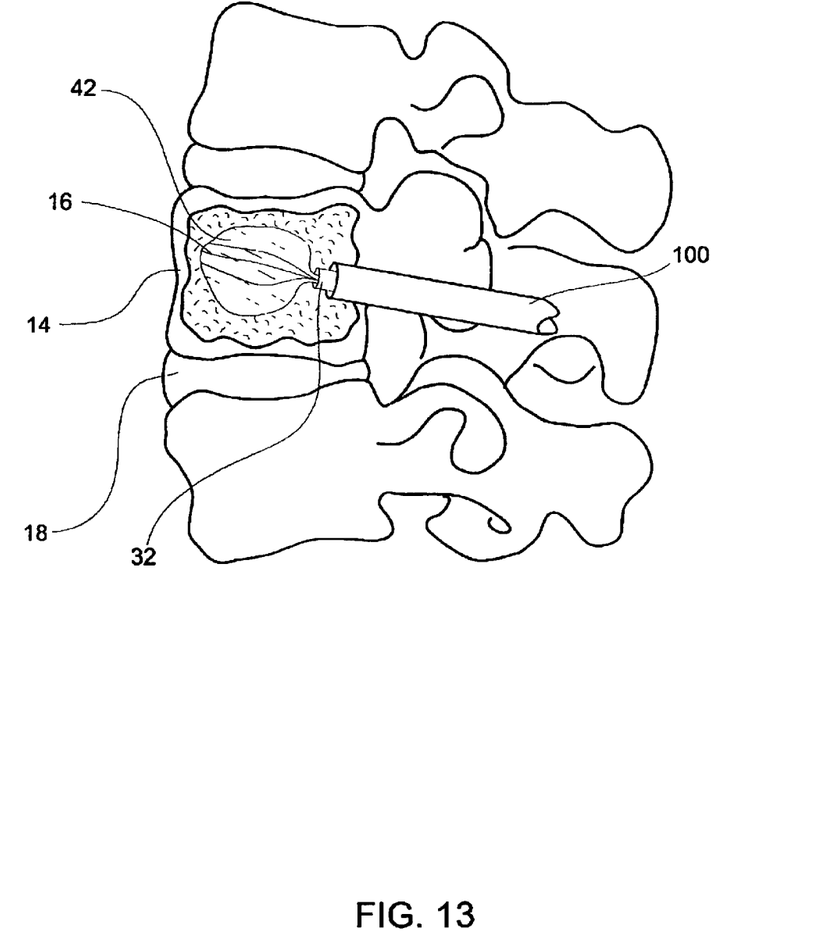
FIG. 13 is a partially cut away side view of the balloon of the apparatus shown in FIG. 3 inserted within a vertebral body so as to form a structural prosthesis therein.

The present apparatus and methods can also be used to repair a collapsed or degenerative vertebral body. For example, depicted in FIG. 13 cannula 100 is passed through an incision into a vertebral body 14. Again, tubular member 32 is passed through cannula 100 so that balloon 42 is disposed within vertebral body 14. Balloon 42 is then filled with the biomaterial so that the balloon 42 compress the bone material therein and fills all voids. If vertebral body 14 is collapsed, balloon 42 is filled to the extent necessary to raise vertebral body 14 to its original height. Once balloon 42 is filled to the proper size and the biomaterial is at least partially cured, the line is used to at least partially sever balloon 42. Tubular member 32 and balloon 42 are then retracted as discussed above leaving the biomaterial to cure into the final structural prosthesis within vertebral body 14.

It is clear from the foregoing that the inventive apparatus and methods have a number of benefits. For example, unlike the prior art prefabricated prostheses which require relative large incisions, balloons 42 and the curable biomaterial can be implanted through minimally invasive incisions, thereby reducing the risk of infection and decreasing patient recovery time. Furthermore, unlike some prior art which requires the use of a degenerative annulus fibrosus 20 as a mold, by using the biomaterial in conjunction with balloon 42, an entire intervertebral disc 18 or portion thereof can be replaced without the required use of annulus fibrosus 20 or the risk of loss of biomaterial by seepage through fissures. Although the present invention is depicted herein for use with a spinal column, it is also appreciated that the present invention can be used in other surgical and non-surgical procedures where it is desired to position in-situ a structural member.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for in-situ formation of a structural prosthesis, the apparatus comprising:

a tubular member having a proximal end and an opposing distal end;

a balloon comprising a wall bounding a compartment, the balloon being coupled with the tubular member such that the tubular member communicates with the compartment of the balloon;

a curable biomaterial disposed within the compartment of the balloon; and means for severing at least a portion of the wall of the balloon after the biomaterial has at least partially cured therein such that the balloon can be selectively removed from around the at least partially cured biomaterial.

2. An apparatus as recited in claim 1, wherein the tubular member comprises a catheter.

3. An apparatus as recited in claim 1, wherein the tubular member comprises a rigid tubular shaft.

4. An apparatus as recited in claim 1, wherein the balloon is integrally formed with or is connected to the tubular member.

5. An apparatus as recited in claim 1, wherein the means for at least partially severing the wall of the balloon comprises a line disposed on the wall of the balloon such that pulling on the line causes the line to at least partially sever the wall of the balloon.

6. An apparatus as recited in claim 1, wherein the means for at least partially severing the wall of the balloon comprises a line disposed on the wall of the balloon such that heating or vibrating the line causes the line to at least partially sever the wall of the balloon.

7. An apparatus for in-situ formation of a structural prosthesis, the apparatus comprising:

a tubular member having a proximal end and an opposing distal end with a passageway extending therebetween;

a balloon comprising a wall bounding a compartment, the balloon being permanently fixed to the tubular member with the passageway of the tubular member being in fluid communication with the compartment of the balloon; and a line mounted on the wall of the balloon, to facilitate at least partial severing of the wall of the balloon.

8. An apparatus as recited in claim 7, wherein at least a portion of the line is embedded within the wall of the balloon.

9. An apparatus as recited in claim 7, wherein at least a portion of the line is secured against the wall of the balloon.

10. An apparatus as recited in claim 7, wherein the line is a wire comprised of metal.

11. An apparatus as recited in claim 7, wherein the line is comprised of a polymer.

12. An apparatus as recited in claim 7, wherein the line has a cutting edge formed thereon.

13. An apparatus as recited in claim 7, wherein the tubular member comprises a catheter.

14. An apparatus as recited in claim 7, wherein the tubular member comprises a rigid tubular shaft.

15. An apparatus as recited in claim 7, wherein the balloon is integrally formed with or is connected to the tubular member.

16. A method for forming a structural prosthesis within an intervertebral disc, the method comprising:

inserting at least a portion of a balloon within a site of an intervertebral disc;

at least partially filling the balloon within the site of the intervertebral disc with a biomaterial;

allowing the biomaterial to at least partially cure; and removing the balloon from around the at least partially cured biomaterial within the site of the intervertebral disc.

17. A method as recited in claim 16, further comprising resecting at least a portion of the nucleus pulposus of the intervertebral disc prior to inserting the balloon.

18. A method as recited in claim 17, further comprising resecting at least a portion of the annulus fibrosus of the intervertebral disc prior to inserting the balloon.

19. A method as recited in claim 16, wherein the act of at least partially filling the balloon with a biomaterial comprises at least partially filling the balloon with a hydrogel or polyurethane.

20. A method as recited in claim 16, wherein the act of at least partially filling the balloon with a biomaterial comprises at least partially filling the balloon with calcium phosphate, calcium sulfate, acrylic, carbonate, or combinations thereof.

21. A method as recited in claim 16, wherein the act removing the balloon comprises at least partially severing a wall of the balloon.

22. A method as recited in claim 21, wherein the act of at least partially severing the wall of the balloon comprises cutting or tearing a portion of the wall of the balloon.

23. A method as recited in claim 21, wherein the act of at least partially severing the wall of the balloon comprises melting a portion of the wall of the balloon.

24. A method comprising:
    inserting at least a portion of a balloon within a vertebral body;
    at least partially filling the balloon within the vertebral body with a biomaterial;
    allowing the biomaterial to at least partially cure; and
    removing the balloon from around the at least partially cured biomaterial within the vertebral body.

25. A method as recited in claim 24, wherein the act of at least partially filling the balloon with a biomaterial comprises at least partially filling the balloon with calcium phosphate, calcium sulfate, acrylic, carbonate, or combinations thereof.

26. A method as recited in claim 24, wherein the act removing the balloon comprises at least partially severing a wall of the balloon.

27. A method as recited in claim 26, wherein the act of at least partially severing the wall of the balloon comprises cutting or tearing the wall of the balloon.

28. A method as recited in claim 26, wherein the act of at least partially severing the wall of the balloon comprises melting a portion of the wall of the balloon.

29. An apparatus for in-situ formation of a structural prosthesis, the apparatus comprising:
    a balloon comprising a wall having an interior surface bounding a compartment, the balloon having a perimeter length;
    a tubular member-having a passageway extending therethrough, the tubular member begin coupled with the balloon so that the passageway of the tubular member is in fluid communication with the compartment of the balloon; and
    a line having a first portion continuously embedded within the wall of the balloon or continuously mounted on the interior surface of the balloon over a distance of at least half the perimeter length of the balloon.

30. An apparatus as recited in claim 29, wherein the line has a second portion longitudinally extending within the passageway of the tube.

31. An apparatus as recited in claim 30, wherein the tubular member has a length and the second portion of the line has a length greater than or equal to the length of the tube.

32. An apparatus as recited in claim 29, wherein the tubular member has a length and the line has a second portion disposed outside of the balloon, the second portion of the line having a length greater than or equal to the length of the tube.

33. An apparatus as recited in claim 29, wherein the tubular member comprises a rigid tubular shaft.

34. An apparatus for in-situ formation of a structural prosthesis, the apparatus comprising:
    a balloon comprising a wall bounding a compartment;
    a substantially rigid tubular member having a passageway extending therethrough, the tubular member being coupled with the balloon so that the passageway of the tubular member is in fluid communication with the compartment of the balloon; and
    a line mounted on the wall of the balloon to facilitate at least partial severing of the wall of the balloon.

35. An apparatus as recited in claim 34, wherein at least a portion of the line is embedded within the wall of the balloon.

36. An apparatus as recited in claim 34, wherein the line is a wire comprised of metal.

37. An apparatus as recited in claim 34, wherein the balloon is movable between a first deflated position wherein at least a portion of the balloon is disposed within the passageway of the tubular member and a second inflated position wherein at least a portion of the balloon is disposed outside of the passageway of the tubular member.

38. An apparatus as recited in claim 34, wherein the tubular member is slidably disposed within a cannula.

39. An apparatus as recited in claim 34, further comprising a curable biomaterial disposed within the compartment of the balloon.

40. An apparatus for in-situ formation of a structural prosthesis, the apparatus comprising:
    a balloon comprising a wall bounding a compartment;
    a tubular member having a passageway extending therethrough, the tubular member begin coupled with the balloon so that the passageway of the tubular member is in fluid communication with the compartment of the balloon, at least a portion of the balloon being disposed within the passageway tubular member; and
    a line mounted on the wall of the balloon to facilitate at least partial severing of the wall of the balloon.

41. An apparatus as recited in claim 40, wherein the tubular member is rigid.

42. An apparatus as recited in claim 40, wherein at least a portion of the line is embedded within the wall of the balloon.

* * * * *

UNITED STATES PATENT AND TRADEMARK OFFICE
CERTIFICATE OF CORRECTION

PATENT NO. : 6,932,843 B2  Page 1 of 1
APPLICATION NO. : 10/255161
DATED : August 23, 2005
INVENTOR(S) : Stephen A. Smith et al.

It is certified that error appears in the above-identified patent and that said Letters Patent is hereby corrected as shown below:

Column 2 Line 57 (drawing descriptions) ADD --curable-- after "with a" and before "biomaterial"

2.61 (drawing descriptions) ADD --removal-- after "severed for" and before "around"

6.2 (detailed description) Delete "of" after "partially" and instead ADD --or--

6.11 (detailed description) Delete "a" preceding "intervertebral disc" and ADD --an--

7.31 (detailed description) Delete "Compress" and ADD --compresses--

9.56 (claim29) Delete "between" and "Member" and "having" Replace Deletions with a SPACE 9.57 (claim 29) Delete "begin" and ADD --being--

Signed and Sealed this

Nineteenth Day of September, 2006

JON W. DUDAS
*Director of the United States Patent and Trademark Office*